US012714412B2

(12) United States Patent
Dooney et al.

(10) Patent No.: US 12,714,412 B2
(45) Date of Patent: Aug. 25, 2026

(54) EXPANDING SURGICAL ANCHOR AND METHOD OF TISSUE REPAIR

(71) Applicant: Arthrex, Inc., Naples, FL (US)

(72) Inventors: Thomas Dooney, Naples, FL (US); Derek Sullivan, Naples, FL (US); Nathanael Gamso, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 523 days.

(21) Appl. No.: 18/146,537

(22) Filed: Dec. 27, 2022

(65) Prior Publication Data

US 2024/0206866 A1 Jun. 27, 2024

(51) Int. Cl.
*A61B 17/04* (2006.01)

(52) U.S. Cl.
CPC ...... *A61B 17/04* (2013.01); *A61B 2017/0409* (2013.01)

(58) Field of Classification Search
CPC ........ A61B 17/0401; A61B 2017/0414; A61B 2017/0409; A61B 2017/0424; A61B 2017/0438; A61B 2017/044; A61B 2017/0432; A61B 2017/0464; A61B 2017/0446; A61B 2017/0448; A61B 2017/045; A61B 2017/0451; A61B 17/0469; A61F 2/0811; A61F 2002/0835; A61F 2002/0858; A61F 2002/0823
See application file for complete search history.

(56) References Cited

U.S. PATENT DOCUMENTS 5,236,445 A 8/1993 Hayhurst et al.
5,336,240 A 8/1994 Metzler et al.
5,464,427 A 11/1995 Curtis et al.
5,545,180 A 8/1996 Le et al.
6,575,976 B2 6/2003 Grafton
7,329,272 B2 2/2008 Burkhart et al.
7,976,565 B1 7/2011 Meridew
8,012,174 B2 9/2011 ElAttrache et al.
9,005,246 B2 4/2015 Burkhart et al.
10,213,240 B2 2/2019 Bryant et al.
11,357,494 B2 6/2022 Denham et al.
(Continued)

OTHER PUBLICATIONS https://www.djoglobal.com/products/active-adaptive/morphix-xt-suture-anchor.
https://www.conmed.com/en-US/home/products/implants-and-suture-anchors/other-fixation/tenolok-dual-expanding-tenodesis-anchor.

*Primary Examiner* — Katherine M Shi
(74) *Attorney, Agent, or Firm* — Blank Rome LLP

(57) ABSTRACT

Expandable surgical anchors and methods of tissue repair with knotless fixation. The method includes coupling a repair strand to tissue to be fixated and inserting an implant with the repair strand that is captured by an implant into a pre-drilled bone hole in an insertion direction. After the implant is inserted into the bone hole, an expanding cannulated fixation device is installed into the bone hole such that the repair strand is positioned outside of the fixation device. After installing the fixation device into the bone hole, the fixation device is expanded by pulling the implant in an activation direction into the fixation device while the fixation device remains stationary, thereby compressing the fixation device against the bone hole with the repair strand disposed between an outer surface of the fixation device and the bone hole and providing tissue fixation without tying any knots.

20 Claims, 11 Drawing Sheets

(56) References Cited

U.S. PATENT DOCUMENTS

| | | | | |
|---|---|---|---|---|
| 11,751,863 | B2 | 9/2023 | Vijay et al. | |
| 2005/0090862 | A1 | 4/2005 | McDevitt et al. | |
| 2010/0292732 | A1 | 11/2010 | Hirotsuka et al. | |
| 2010/0331881 | A1 | 12/2010 | Hart | |
| 2017/0215867 | A1 | 8/2017 | Arai et al. | |
| 2017/0265854 | A1* | 9/2017 | Heaven .............. | A61B 17/0401 |
| 2021/0059808 | A1 | 3/2021 | Diduch et al. | |
| 2021/0177396 | A1 | 6/2021 | Heaven et al. | |
| 2021/0282918 | A1 | 9/2021 | Ticker | |
| 2021/0361280 | A1 | 11/2021 | Heaven et al. | |
| 2022/0338856 | A1* | 10/2022 | Patel .................. | A61B 17/0401 |

* cited by examiner 130
133
136
138
134
134
132

104
139
131
136
132
134
134
130
138

EXPANDING SURGICAL ANCHOR AND METHOD OF TISSUE REPAIR

BACKGROUND

The present disclosure relates generally to surgical anchors and more particularly to expanding type suture anchors and methods of tissue repair using the same with knotless fixation.

When soft tissue tears away from bone, reattachment becomes necessary. Reattachment of soft tissue to bone typically requires the surgeon to implant suture anchors into the bone such that the suture anchors and the repair sutures connected to the tissue are fixed and do not loosen from the bone. Current suture anchors fixate the suture to the bone by threading or interference fit between the anchor and bone. These anchors achieve suture fixation mostly at the cortical regions of the bone where it is dense, sacrificing suture fixation at the cancellous bone where it is less dense.

SUMMARY

The present disclosure provides a method of tissue repair with knotless fixation, that comprises the steps of coupling at least one flexible repair strand to tissue to be fixated; inserting an implant with at least one flexible repair strand captured by the implant into a pre-drilled bone hole in an insertion direction toward a bottom of the bone hole; after inserting the implant into the bone hole, installing an expanding cannulated fixation device into the bone hole, such that the flexible repair strand is positioned outside of the fixation device; and after installing the fixation device into the bone hole, expanding the fixation device by pulling the implant in an activation direction opposite to the insertion direction into the fixation device while the fixation device remains stationary, thereby compressing the fixation device against the bone hole with the flexible repair strand disposed between an outer surface of the fixation device and the bone hole and providing tissue fixation without tying any knots.

In an embodiment of the method, the implant is pulled in the activation direction by pulling on a flexible activation strand threaded through an eyelet in a proximal end section of the implant that faces a top of the bone hole, and the flexible repair strand is captured by threading the flexible repair strand through an eyelet in a distal end section of the implant that faces the bottom of the bone hole.

In some embodiments of the method, the fixation device expands when the implant is pulled in the activation direction and an outer most diameter of the implant engages and pushes out one or more expandable portions of the fixation device; the expandable portions of the fixation device are formed by one or more longitudinal slots in a body of the fixation device; and/or the outer most diameter is between proximal and distal end sections of the implant, and each of the proximal and distal end sections has an eyelet. The method may further comprise the step of threading another flexible repair strand through the eyelet in the proximal end section of the implant and/or the step of locking the other flexible repair strand to the proximal end section of the implant and/or the steps of preloading the fixation device on a shaft of an inserter and releasably attaching the implant to a distal end of the inserter.

In other embodiments, the another flexible repair strand is locked by threading a free end thereof through a splice in the another flexible repair strand; when pulling the implant in the activation direction, the implant and the fixation device are axially aligned; and/or the at least one flexible repair strand is captured by threading the at least one flexible repair strand through an eyelet of the implant and, once the fixation device is expanded by pulling the implant into the fixation device, the eyelet of the implant remains outside of fixation device.

In one embodiment, the implant is a soft anchor and the at least one flexible activation strand is threaded through the soft anchor, the soft anchor bunches when the activation strand is pulled in the activation direction, and the soft anchor is a sleeve and the activation strand extends through an inside of the sleeve, and the flexible repair strand engages an outside of the sleeve.

Another aspect of this disclosure is a surgical anchor that comprises an implant that has a proximal end section configured to engage an end of an inserter, a distal end section configured to engage one or more flexible repair strands, and an expander section between the proximal and distal end sections. The proximal end section of the implant is configured to capture one or more flexible activation strands, and wherein the expander section of the implant has a substantially frusto-conical shape that tapers outwardly toward the distal end section and defines an outer most diameter of the implant. An expanding cannulated fixation device is configured to be loaded on the inserter and to engage the implant, the fixation device having one or more expandable portions configured to allow the fixation device to expand outwardly when the implant is received in the fixation device and the expander section of the implant forces the one or more expandable portions outwardly.

In certain embodiments, the proximal end section of the implant includes an eyelet for capturing the one or more flexible activation strands; the distal end section of the implant includes an eyelet for capturing the one or more flexible repair strands; the size of the eyelet in the distal end section of the implant is at least about twice the size of the eyelet in the proximal end section; the expandable portions are formed by one or more longitudinal slots in a body of the fixation device; the one or more flexible repair strands are threaded through an eyelet of the implant and are positioned outside of a body of the fixation device; an outer surface of the fixation device has bone gripping features; and/or the one or more flexible repair strands is suture or suture tape.

In one embodiment, a method of attaching soft tissue to bone with knotless fixation, comprises the steps of installing a first plurality of anchors in a first medial row and installing a second plurality of anchors in a second lateral row, wherein at least one of the first or second plurality of anchors is the surgical anchor of the disclosure.

In another embodiment, a method of attaching soft tissue to bone with knotless fixation using the surgical anchor of the present disclosure, comprises the steps of inserting an anchor with a length of suture attached thereto into a first hole in the bone; passing the suture attached to the first anchor up through the soft tissue; positioning the implant with a free end of the suture threaded through an eyelet of the implant over a second hole in the bone and inserting the implant into the second hole in the bone; and installing the fixation device into the second hole in the bone, over the implant, to secure the suture in the second hole without tying any knots, such that the securing of the suture in the second hole is knotless. The method may further comprise the step of retrieving the suture through a cannula after the suture is passed up through the soft tissue, after retrieving the suture through the cannula, inserting the end of the suture through the eyelet of the implant. The method may also include the step of tensioning the suture.

This summary is not intended to identify essential features of the claimed subject matter, nor is it intended for use in determining the scope of the claimed subject matter. It is to be understood that both the foregoing general description and the following detailed description are exemplary and are intended to provide an overview or framework to understand the nature and character of the disclosure.

BRIEF DESCRIPTION OF THE FIGURES

The accompanying drawings are incorporated in and constitute a part of this specification. It is to be understood that the drawings illustrate only some examples of the disclosure and other examples or combinations of various examples that are not specifically illustrated in the figures may still fall within the scope of this disclosure. Examples will now be described with additional detail through the use of the drawings, in which.

DETAILED DESCRIPTION

The expanding surgical anchors and methods of tissue repair of the present disclosure incorporate additional fixation other than that of conventional suture anchors after the anchor has been implanted in bone. The anchors of the present disclosure are designed to maintain cortical bone fixation while also taking advantage of expanding and locking into the cancellous bone for additional fixation. The surgical anchors and methods of repair of the present disclosure fixate the repair strand, e.g. suture, at the cortical region of the bone but also expands the anchor within the cancellous region of the bone to compact the bone and increase the suture fixation in the compacted bone.

Figure 7A:
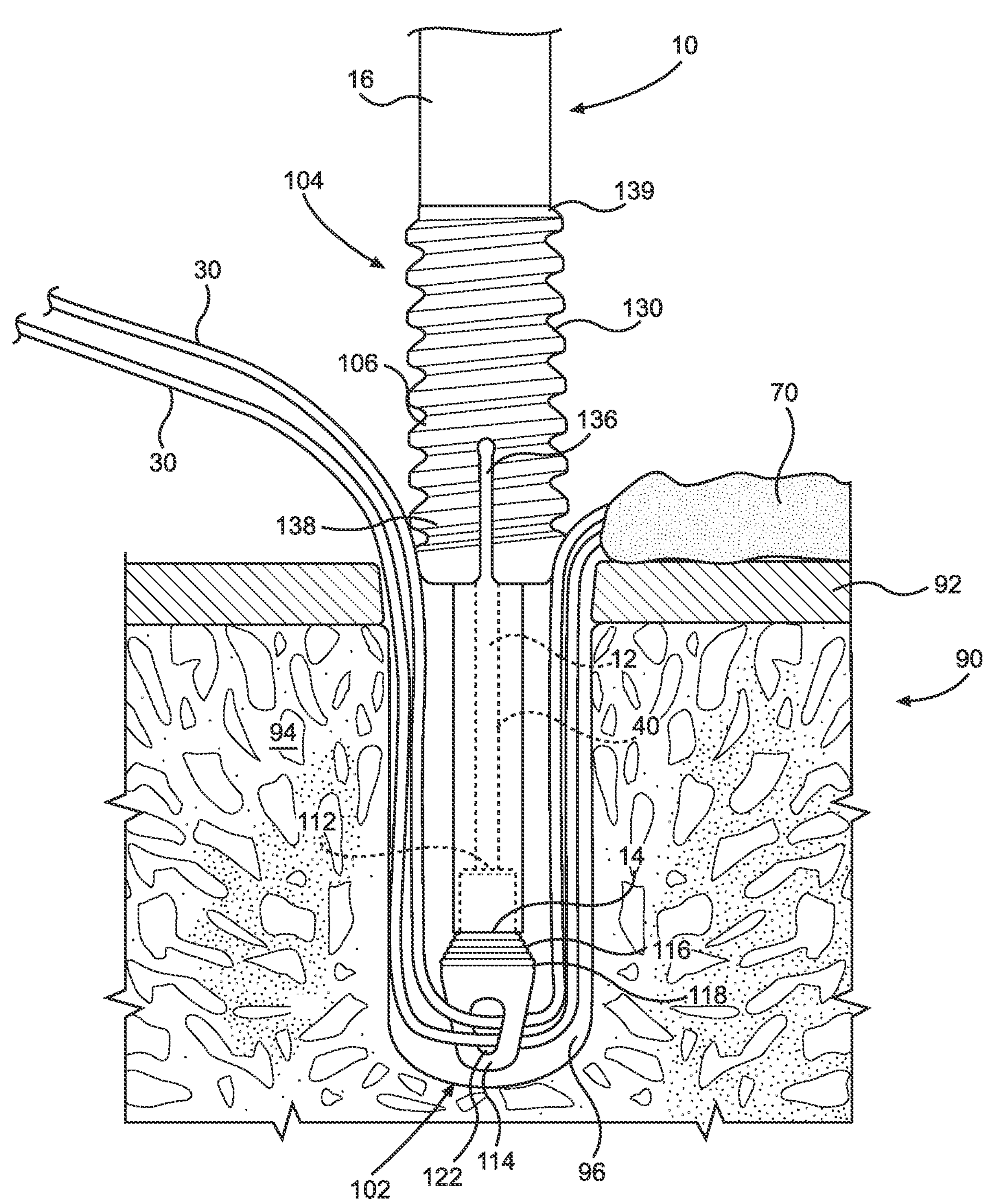
FIGS. 7*a* thru 7*e* illustrates the steps in an exemplary method of tissue repair using the surgical anchor illustrated in FIG. 1.
Figure 7B:
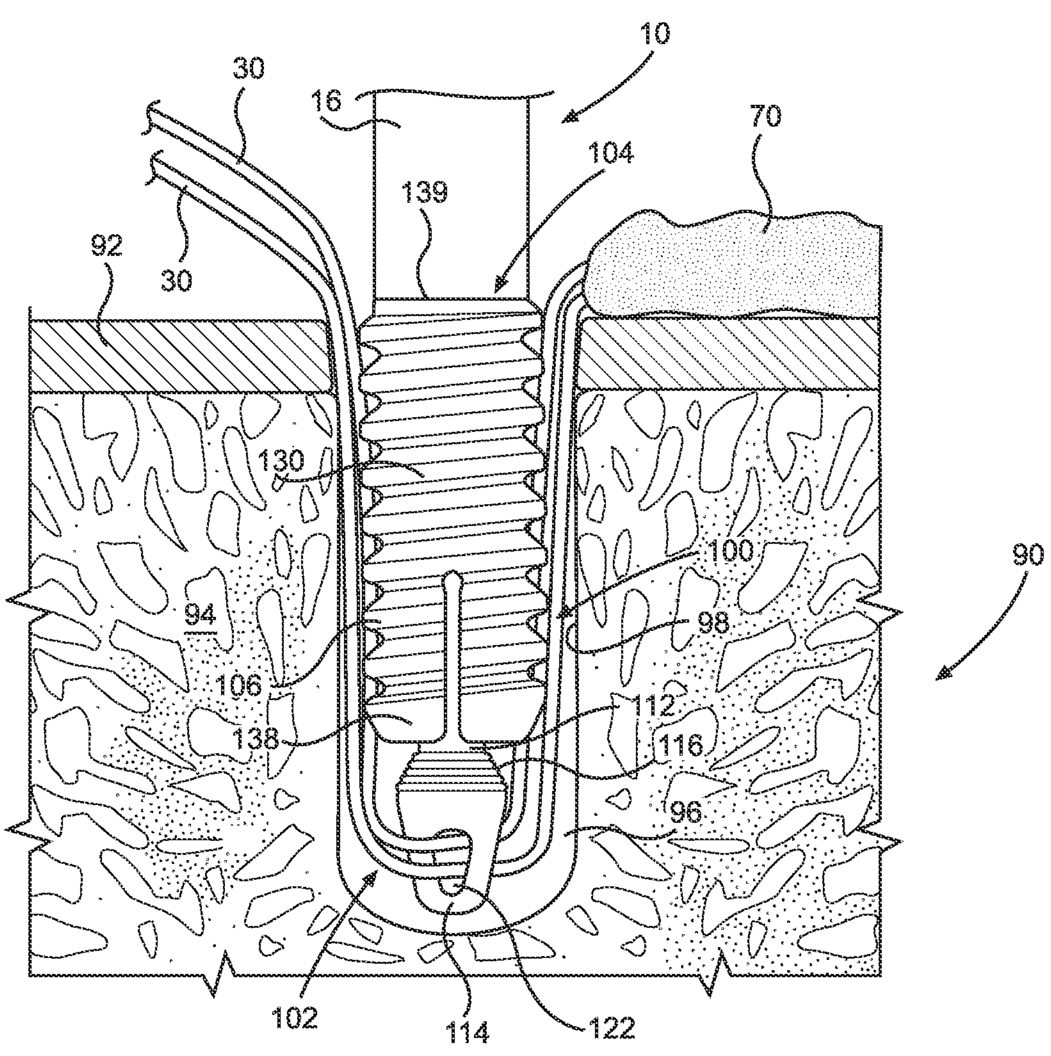
Figure 7C:
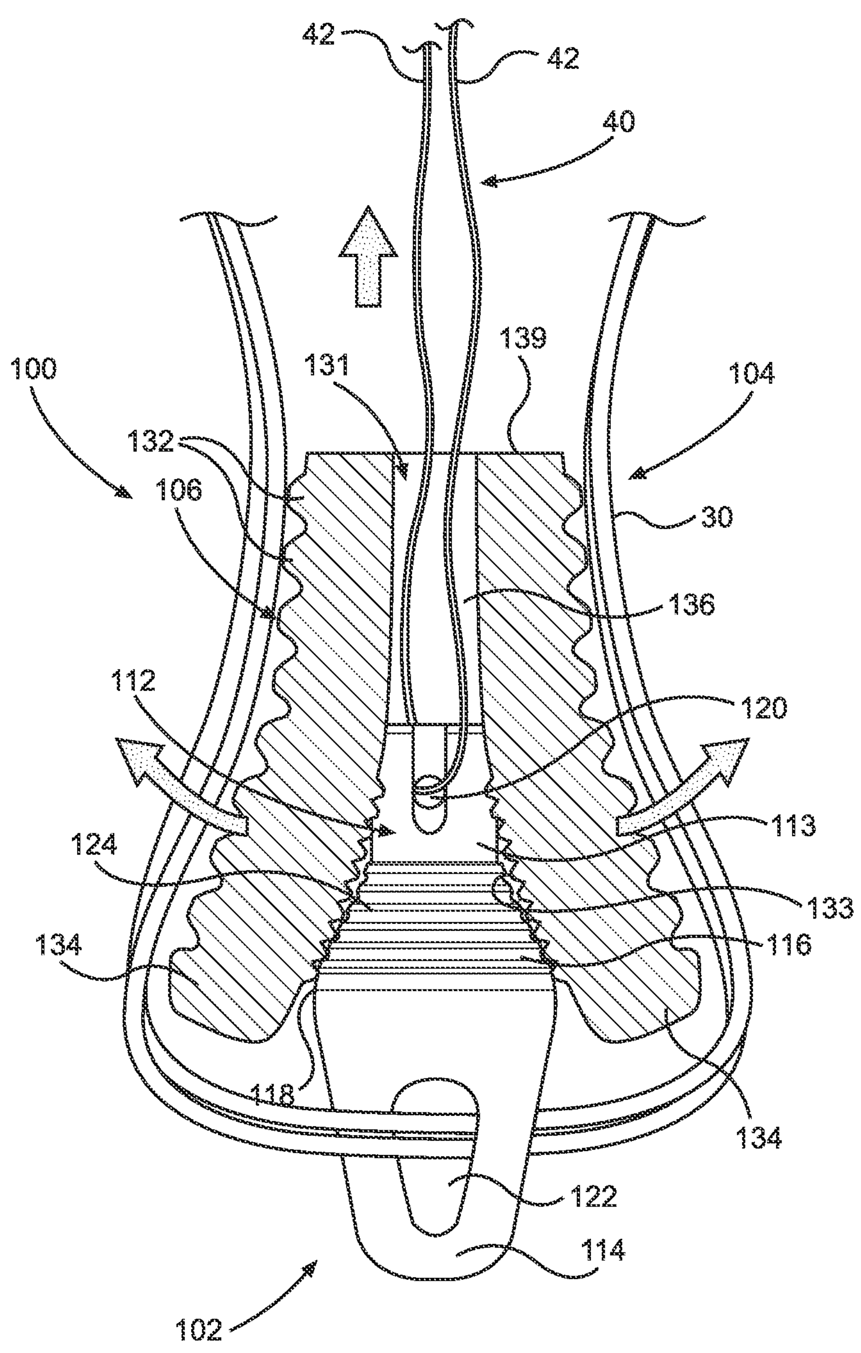
Figure 7D:
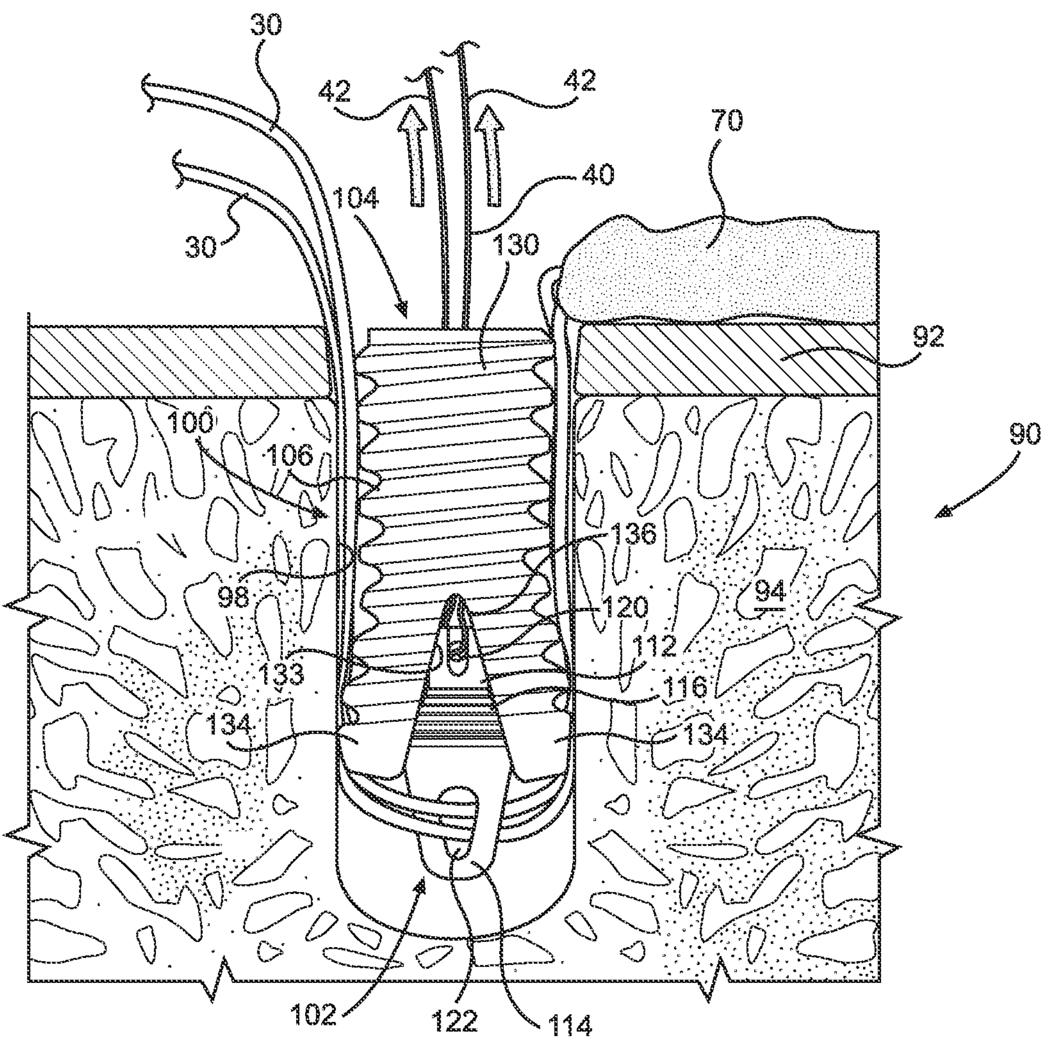
Figure 7E:
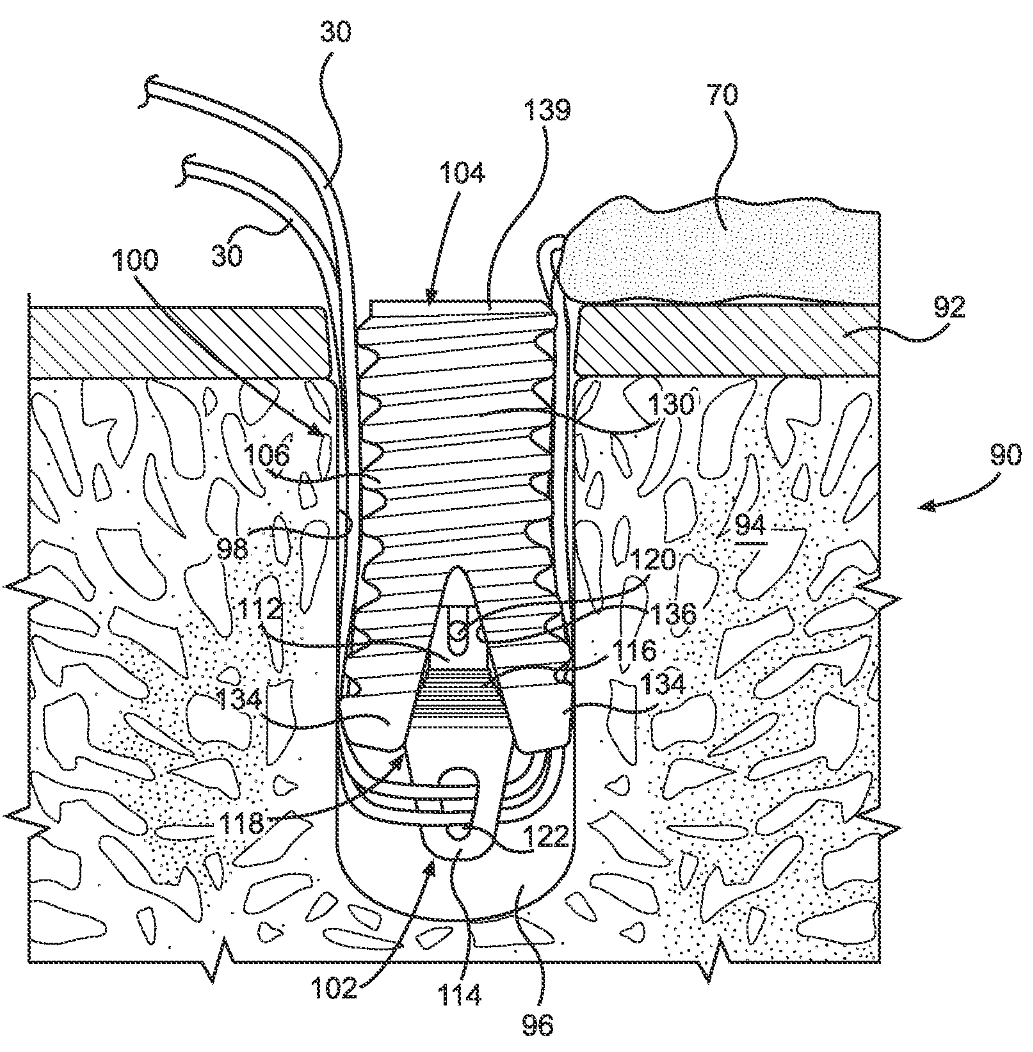
Figure 8A:
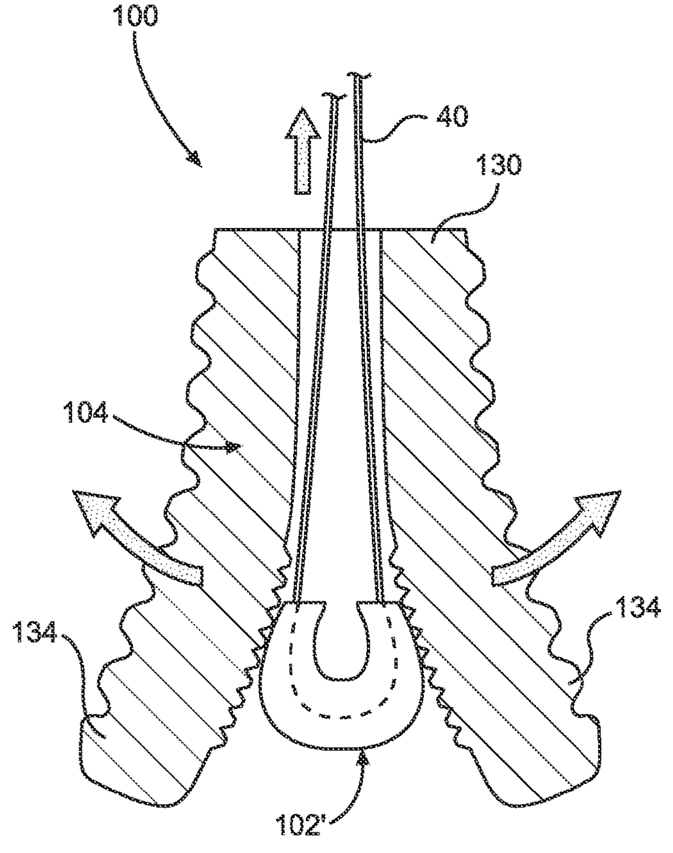
FIGS. 8*a* and 8*b* are elevational views of an exemplary surgical anchor according to another embodiment.
Figure 8B:
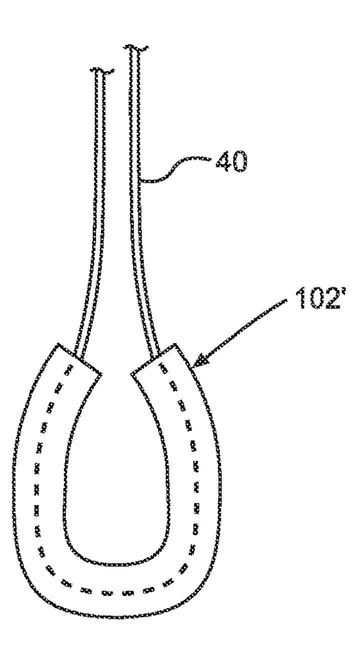

Referring to the figures, a surgical anchor 100 according to an exemplary embodiment of the present disclosure generally includes an implant 102 that captures one or more flexible repair strands 30 (also referred to as "primary repair strand") and a fixation device 104. The implant 102 is configured to be received in and expand the fixation device 104 such that the primary repair strand or strands 30 (which are coupled to the soft tissue 70) are fixed in the bone 90 between an outer surface 106 of the fixation device 104 and the inner surface 98 of the hole 96 pre-drilled in bone 90. The surgical anchor 100 is adapted to fix to the bone 90 and both the cortical region 92 and the cancellous region of the bone 90, as seen in FIG. 7*e*, for positive tissue o bone contact.

In an example, the anchor 100 includes a cannulated and slotted expandable anchor body 130 and the expander/implant 102 can be retracted into the anchor body 130 to expand the anchor 100 after installation in the bone hole. The implant 102 includes a proximal eyelet 120 at its proximal end that receives one or more flexible activation strands 40 for pulling the implant 102 back through the body of the anchor. The anchor body 130 may include outer ridges 132 for engaging the bone inside the bone hole. The anchor body 130 may also have inner teeth at its distal end for engaging corresponding teeth on an angled proximal ledge of the implant. To secure the anchor to bone, the limbs 42 of the activation strand 40 (connected to the proximal eyelet 120 at the proximal end of the implant) are pulled back in line or coaxial with the anchor body 130 to retract the implant 102 into the anchor body 130, thereby expanding the distal end of the implant 102 into the cancellous bone 94.

Figure 1:
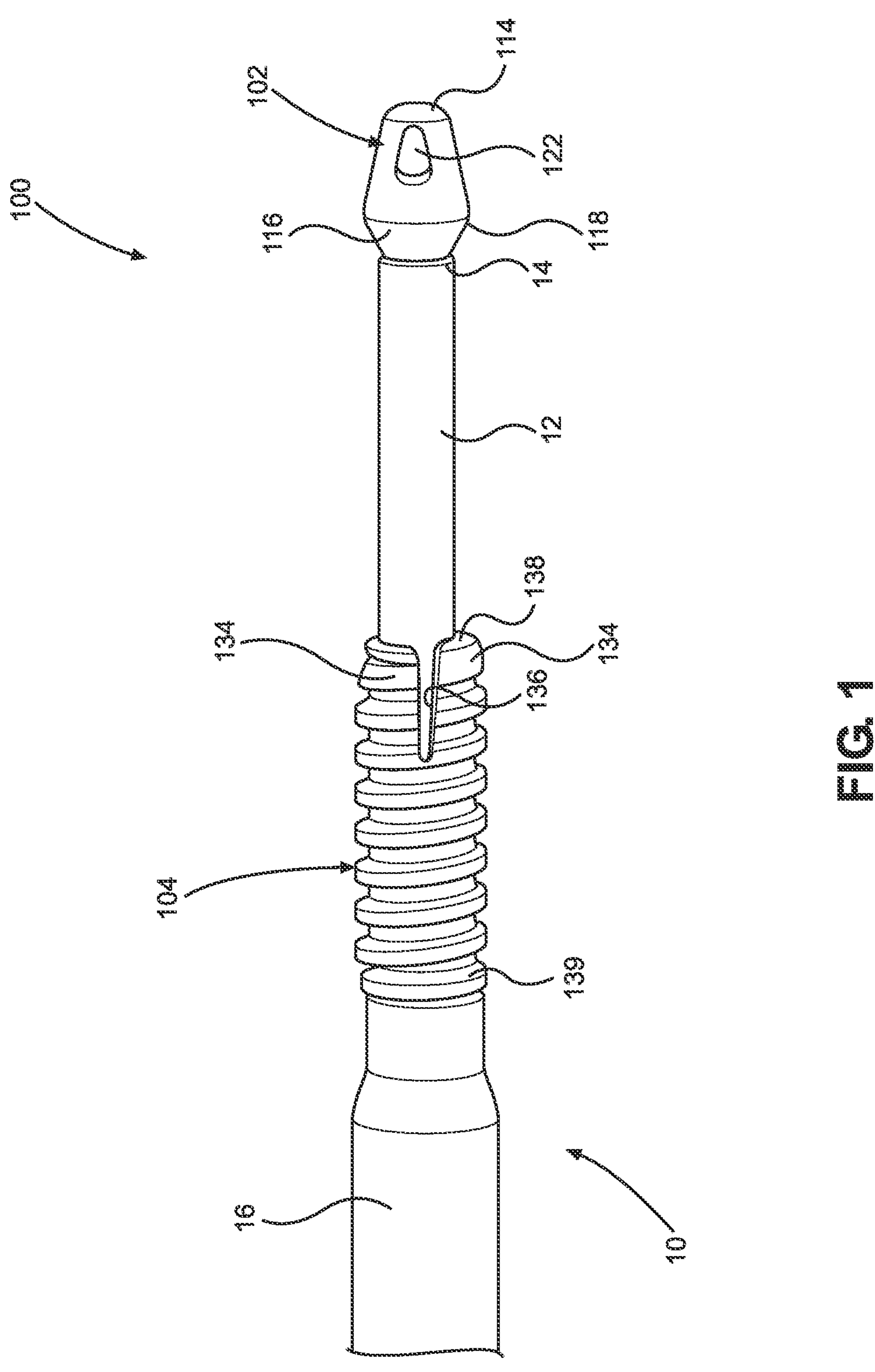
FIG. 1 is an elevational view of an exemplary surgical anchor according to one example, showing the expanding suture anchor loaded on an inserter.
Figures 2, 3:
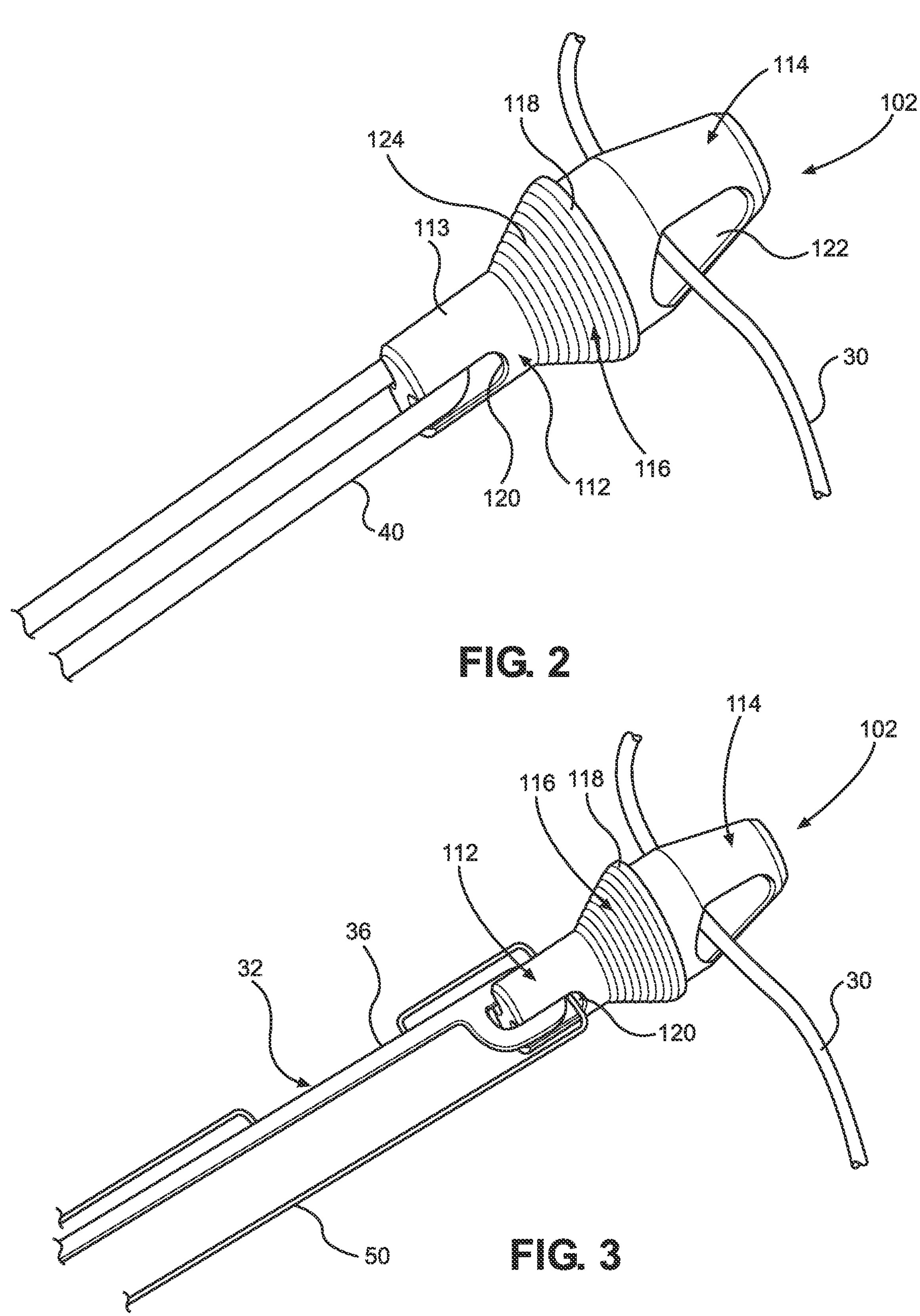
FIG. 2 is a perspective from a proximal end of an exemplary implant of the surgical anchor of FIG. 1.
FIG. 3 is another perspective view of the implant of the surgical anchor illustrated in FIG. 1.

The implant 102 has a proximal end section 112, a distal end section 114, and an expander section 116 therebetween, as seen in FIGS. 1-3. The proximal end section 112 is configured to releasably engage an end or tip 14 of an inserter 10. For example, the proximal end section 112 can have a reduced diameter portion 113 that allows the proximal end section 112 to be slidably inserted into the tip 14 of a cannulated rod 12 of the inserter 10, as seen in FIG. 7*a*. Any releasable engagement can be used to couple the proximal end section 112 of the implant 102 with the tip 14 of the inserter 10. The proximal end section 116 of the implant 102 can also be configured to capture one or more flexible activation strands 40 (also referred to as "activation strand"). For example, an aperture, notch, or eyelet 120 (also referred to as "proximal eyelet") can be incorporated into the proximal end section 112 of the implant 102. The proximal eyelet 120 is sized to receive the activation strand 40. The limbs 42 of the activation strand 40 can extend through the cannulated rod 14 of the inserter 10 when loading the implant 102 onto the inserter 10. The proximal eyelet 120 may also receive one or more secondary flexible repair strands 32 (also referred to as "secondary repair strand") that may be used to secure the tissue 70 to bone 90 in addition to the primary repair strand 30.

The distal end section 114 of the implant 102 is configured to engage the primary repair strand or strands 30. For example, an aperture, notch, or eyelet 122 (also referred to as the "distal eyelet") can be incorporated into the distal end section 114 of the implant 102. The distal eyelet 122 is sized to receive the primary repair strand or strands 30. The proximal eyelet 120 and the distal eyelet 122 of the implant 102 can be different sizes and/or shapes or can be substantially the same size and/or substantially the same shape. In an example, the distal eyelet 122 is circular and about at least twice the size of the circular proximal eyelet 120, as seen in FIG. 7*c*.

The expander section 116 of the implant 102 can have, for example, a substantially frusto-conical shape that tapers outwardly toward the distal end section 114 and defines an outer most diameter 118 of the implant 102, as seen in FIGS. 2 and 3. The outer most diameter 118 is sized to engage and expand the fixation device 104. The outer surface 124 of the expander section 116 may be textured or grooved with ribs, teeth knurls, or the like.

The distal eyelet 122 of the implant 102 is configured to receive the primary repair strand or strands 30. The primary repair strands 30 may be any known flexible strand suitable for use in a surgical repair procedure, such as suture or suture tape, for example. The secondary repair strand or strands 32 can be provided at the proximal end section 112 of the implant 102. The second repair strand 32 can pass through the same proximal eyelet 102 as the activation strand 40 at the proximal end section 112 of the implant 102. This secondary repair strand 32 can be fixed to the proximal eyelet 120 via a locking splice 36 by using a passing device or shuttle 50 to thread the secondary repair strand 32 through itself at the splice 36, as seen in FIG. 3, thereby fixing the secondary repair strand 32 in place. When repairing the tissue, the surgeon can use either or both the primary and secondary repair strands 30 and 32, and the strands 30 and 32 can be used for the same or different repair purposes.

The fixation device 104 includes an anchor body 130 that is cannulated for loading the fixation device 104 on the inserter 10. The outer surface 106 of the anchor body 130 may have bone gripping features 132, such as threads, barbs, ribs, teeth, or the like, to engage the inner surface 98 of the bone hole 96. The fixation device 104 is configured to expand when the implant 102 is pulled into the cannulation 131 of the anchor body 130. The fixation device 104 can be designed to be expandable by including slots, cuts, recess, grooves, or the like in the anchor body 130. In an example, the fixation device 104 has one or more expandable portions 134 configured to allow the fixation device 104 to expand outwardly when the implant 102 is received in the anchor body 130 of the fixation device 104, as seen in FIG. 7*c*, and the implant's outer most diameter 118 engages the inner surface 133 of the fixation device 104. The expandable portions 134 can be formed by one or more longitudinal slots 136 in the anchor body 130 wherein the slots 136 open at a distal end 138 of the anchor body 130. The proximal end 139, opposite the distal end 138, of the anchor body 130 is adapted to engage or abut an outer shaft 16 of the inserter 10, as seen in FIG. 1.

In an embodiment, the anchor body 130 is fully cannulated and the outer surface 106 can either be threaded or barbed for fixation into the bone. And there are at least two of the longitudinal slots 136 which can extend from the distal end 138 of the anchor body 130 allow for the anchor expansion via portions 134 at the distal end 138. In an example the longitudinal slots 136 can run about ¾ of the length of the anchor body 130.

Figure 5:
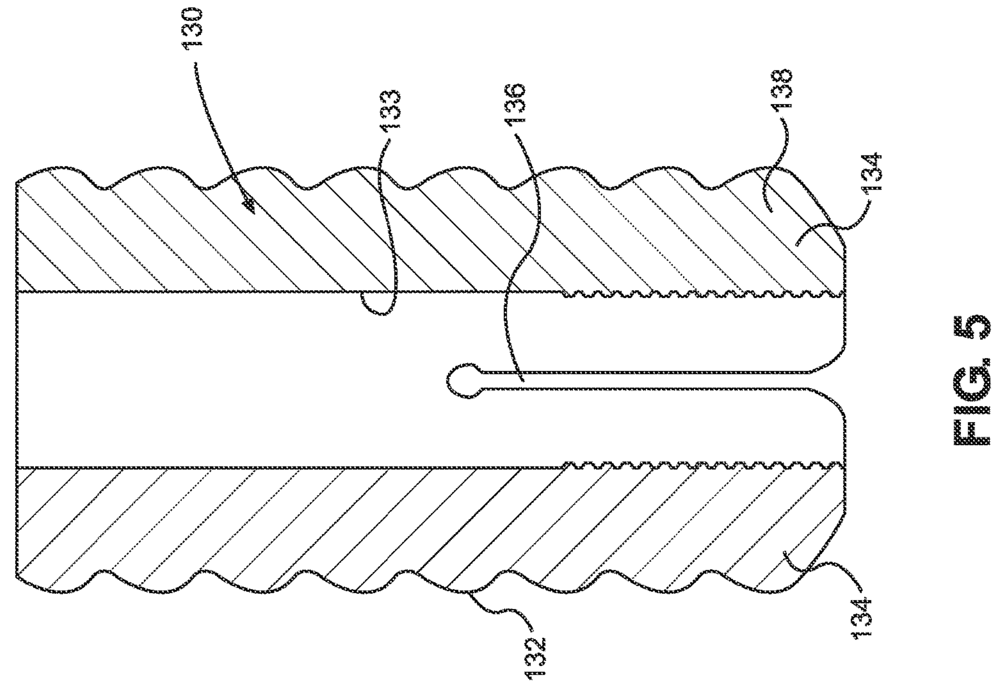
FIG. 5 is a cross-sectional view of the fixation device illustrated in FIG. 4.
Figure 4:
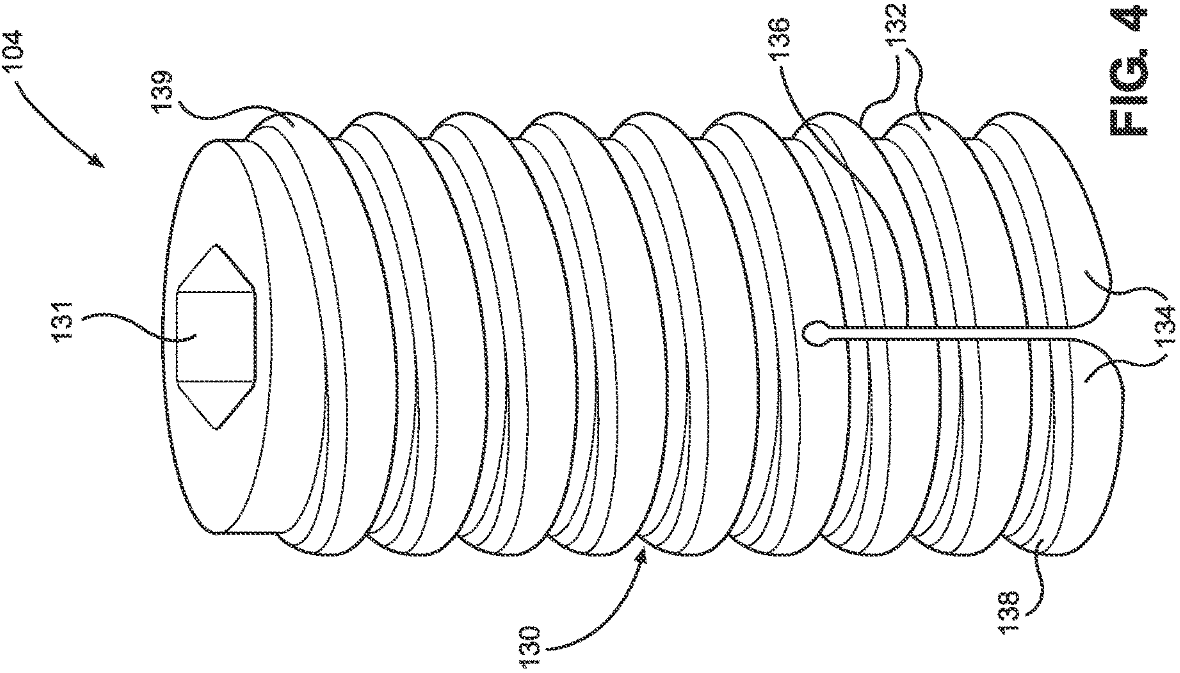
FIG. 4 is a side elevational view of an exemplary fixation device of the surgical anchor illustrated in FIG. 1

The top or closed end of each longitudinal slot 136 can be radiused or curved, as seen in FIG. 4, to prevent the expanding slot from propagating through the anchor body 130 and to avoid snagging of the repair strands. The bottom of the slots 136 at the distal end 138 of the anchor body 130 can be rounded or beveled to allow the repair strands to freely slide past the anchor body 130 during anchor expansion. FIG. 5 illustrates a cross-section of the anchor body 130 of the fixation device 104, showing the cannulation 131 and one of the slots 136. The inner surface 133 of the anchor body 130 can optionally include an internal texture or teeth at or near the distal end 138 of the anchor body 130.

Figure 6B:
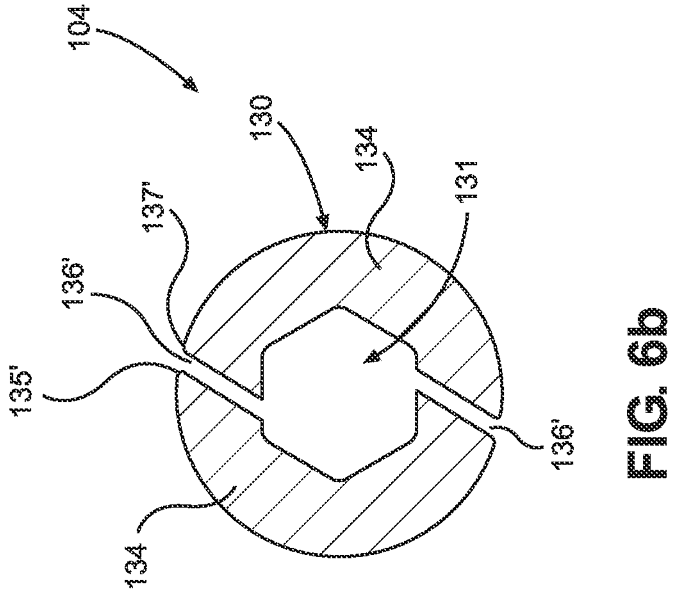
FIGS. 6*a* and 6*b* are cross-sectional views of alternative examples of the body of the fixation device illustrated in FIG. 4.
Figure 6A:
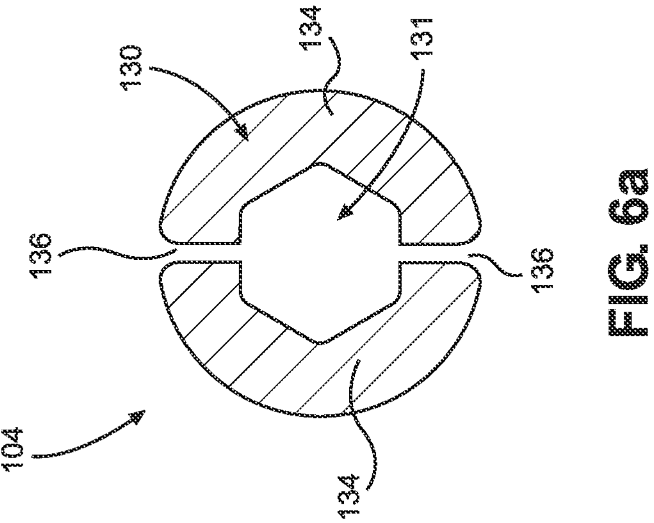

Each longitudinal slots 136 can also be vertical or offset at an angle, as seen in FIGS. 6*a* and 6*b*, respectively. As seen in FIG. 6*a*, the slots 136 are oriented vertically or straight with respect to the length of the anchor body 130. The longitudinal slots 136 can extend generally parallel to the central longitudinal axis of the fixation device 104.

As seen in FIG. 6*b*, the longitudinal slots 136' can be cut at an angle to help close the slots while turning the fixation device 104 into bone. This will help prevent any sharp edges of the anchor body 130 from catching on the bone and breaking the fixation device 104 when installing the device 104. Also, by angling the slots 136', the sharp or acute angled corner 135' of each slot 136' will not engage the repair strand 30 as it is turning away from the repair strand 30 during insertion of the fixation device 104, and the opposite non-sharp or obtuse angled corner 137' of each slot 136' will not engage the repair strand as the anchor body 130 turns toward the repair strand 30 during insertion of the fixation device 104.

A method of tissue repair using the surgical anchor 100 can be for a single attachment or a single row of attachments (anchor-to-tissue) or a double row (e.g., medial and lateral rows) of attachments (anchor to anchor).

To load the inserter 10 with the surgical anchor 100, the cannulated body 130 of the fixation device 104 is first inserted onto cannulated rod 12 of the inserter 10 and then seated on a shaft end of the inserter 10, similar to disclosure of U.S. Pat. No. 8,012,174, the subject matter of which is herein incorporated by reference. The limbs 42 of the activation strand 40 extending from the proximal eyelet of the implant 102 are threaded through the cannulation of the rod 12 of the inserter 10. Subsequently, the implant 102 is seated on the distal tip 14 of the inserter 10.

An exemplary method of tissue repair of the present disclosure can be accomplished with knotless fixation and comprising the steps of coupling the flexible repair strand 30 to the tissue 70 to be fixated and inserting the implant 102 with the flexible repair strand 30 captured in the distal eyelet 122 of the implant 102 into the pre-drilled bone hole 96 in an insertion direction toward the bottom of the bone hole. As seen in FIG. 7*a*, the primary repair strands 30 are fed through the distal eyelet 122 of the implant 102. In an embodiment of the present disclosure, the primary repair strand 30 is passed through the tissue or graft at desired points. The cannulated anchor body 130 of the fixation device 104 is pre-loaded onto the inserter 10 provided with the implant 102 at its distal end or tip 14. The repair strand 30 attached to the tissue or graft are passed through the distal eyelet 122 of the implant 102. The distal end of the inserter 10 together with the implant 102 can be inserted directly into the pre-drilled hole 96 in the bone 90. The inserter 10 may be rotated (in a clockwise direction, for example) to advance the fixation device 104 over proximal end section 112 of the implant 102. The eyelet 122 is then positioned at the bottom of the prepared or pre-drilled bone hole 96. The surgeon has the option of adjusting the tensioning the repair strands at this time.

After inserting the implant 102 into the bone hole 96, the expanding cannulated fixation device 104 is installed into the bone hole 96 such that flexible repair strand 30 is positioned outside of the fixation device 104. As seen in FIG. 7*b*, the anchor body 130 is inserted until flush with the cortical bone 92. The primary repair strands 30 are secured between the anchor body 130 and cortical bone 92. They are partially fixated by the interference with the cancellous bone. The inserter 10 can then be removed, leaving behind the repair strands 30 connected to the distal eyelet 122 of the implant 102.

After installing the fixation device 104 into the bone hole 96, the fixation device 104 is expanded by pulling the implant 102 in an activation direction, as seen in FIG. 7*c*, opposite to the insertion direction into the cannulation 131 of the fixation device 104 while the fixation device 104 remains stationary. The limbs 42 of the activation strand 40, which connect to the proximal eyelet 120 of the implant 102, are pulled back in line with the anchor body 130, as seen in FIGS. 7*c* and 7*d*. The implant 102 is pulled in the activation direction by pulling on the activation strand threaded through the proximal eyelet 120 of the implant 102 that faces the top of the bone hole 96 and wherein the repair strand 30 is captured by threading the repair strand 30 through the distal eyelet 122 in of the implant 102 that faces the bottom of the bone hole 96.

When the implant 102 is pulled into the anchor body 130 in the activation direction, the outer most diameter 118 of the implant 102 forces out and compresses the expandable portions 134 of the fixation device 104 against the inner surface 98 of the bone hole 96 with the repair strand or strands 30 disposed between the outer surface 106 of the fixation device 104 and the bone hole 96, thereby providing tissue fixation without tying any knots. Once the fixation device 104 is expanded by pulling the implant 102 into the fixation device, the distal eyelet 122 of the implant 102 may remain outside of fixation device 104. A knot pusher or stout device can be placed against the proximal end 139 of the anchor body 130 to prevent the anchor body 130 from pulling out of the bone while tensioning the repair strands 30. As seen in FIG. 7*e*, once the anchor 100 is fixed in place, the activation strand 40 can be removed and the remaining limbs of the repair sutures can be tensioned and cut, thereby finalizing the repair.

Another method of tissue repair of the present disclosure includes inserting a first anchor, which can be any type of known anchor, with a length of a repair strand or strands 30 attached thereto into a first pre-drilled hole in the bone and then passing the repair strand 30 attached to this first anchor up through the soft tissue, in a manner similar to the method disclosed in U.S. Pat. No. 8,012,174. The implant 102 of a second anchor, which is surgical anchor 100, is loaded on the inserter 10, and is positioned with the repair strand 30 threaded through the distal eyelet 122 of the implant 102 over a second pre-drilled hole in the bone and the implant 102 is inserted into the second hole in the bone; and installing the fixation device 104 into the second hole in the bone, over the implant 102, to secure the repair strand or strands 30 in the second hole without tying any knots, in the same manner discussed above. The method may also include the steps of retrieving the repair strand 30 through a cannula after the repair strand 30 is passed up through the soft tissue 70, and after retrieving the repair strand 30 through the cannula, inserting the end of the repair strand 30 through the distal eyelet 122 of the implant 102.

Another exemplary method of the present disclosure may include the steps of installing a first plurality of anchors in a first medial row and installing a second plurality of anchors in a second lateral row wherein one or more of the first or second plurality of anchors is the surgical anchor 100, similar to the method disclosed in U.S. Pat. No. 8,012,174.

Figures 9A, 9B, 9C:
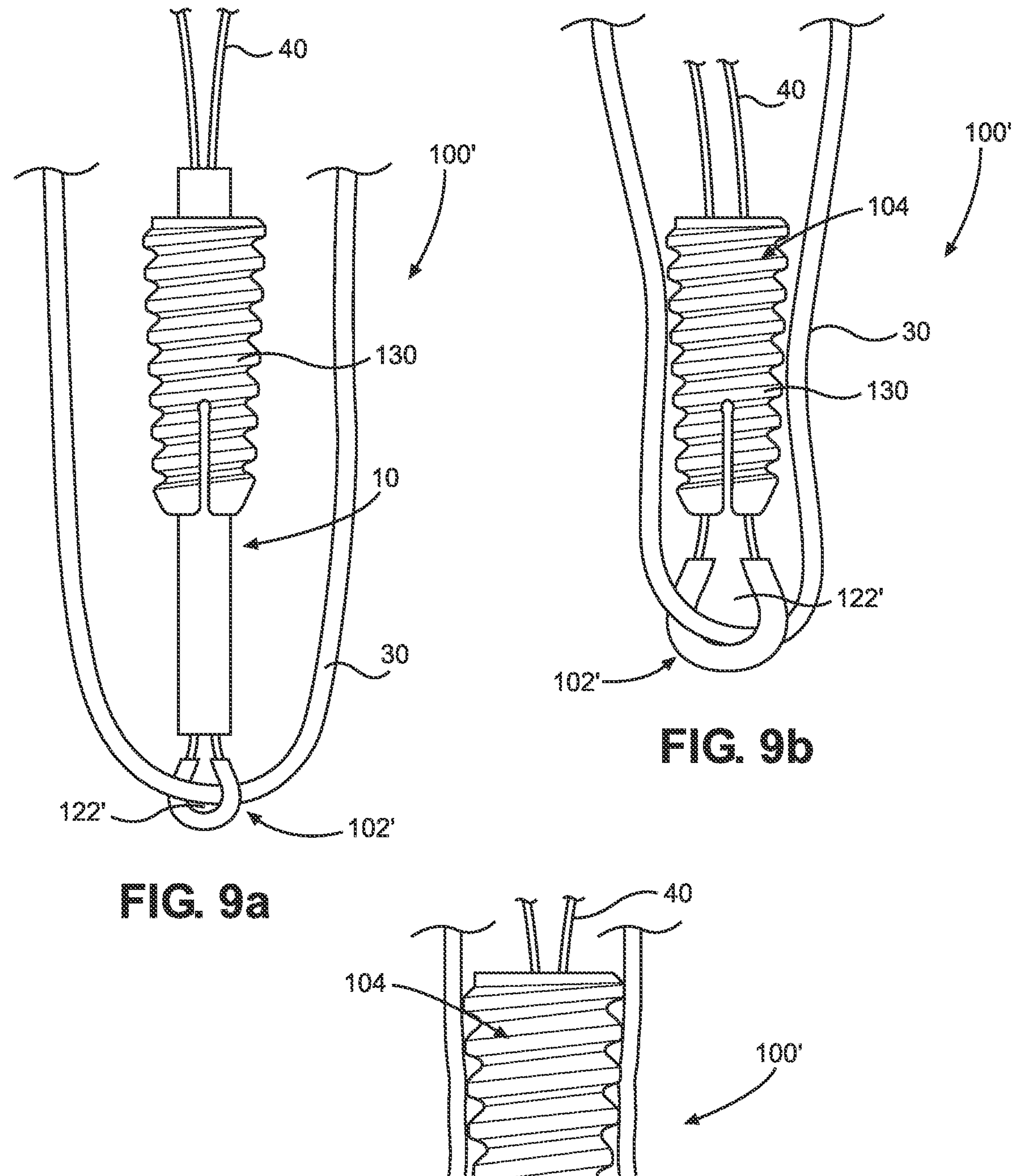
FIGS. 9*a*-9*c* illustrate the steps of another exemplary method of tissue repair using the surgical anchor illustrated in FIGS. 8*a* and 8*b*.

FIGS. 8*a*, 8*b* and 9*a* thru 9*c* illustrate a surgical anchor 100' according to an alternative embodiment of the present disclosure. The surgical anchor 100' includes an implant 102' which is a soft anchor, such as a sleeve or sheath, formed of a bunching material. The flexible activation strand 40 is threaded through the inside of the implant 102' such that the implant 102' bunches when the activation strand 40 is pulled in the activation direction, as seen in FIG. 9*c*. The bunching of the implant 102' inside of the anchor body 130 forces the expandable portions 134 of the anchor body 130 to expand outwardly and engage the bone. The repair strand 30 engages an outside of the sleeve implant 102'. For example, the repair strand 30 can be threaded through an eyelet 122' that is created by looping or folding the implant 102', as seen in FIG. 9*a*.

Suture or suture tape can be the flexible repair strands used with the anchor to fix tissue to bone. However, the anchor of the disclosure can be used with any type of flexible material or suture. Alternatively, an allograft or biological component may be used instead of suture or tape. The allograft or biological component may be comprised of tendon or pericardium, for example, which provides improved tissue repair. And any combination of suture, suture tape, and allograft or biological component may be employed, depending on the characteristics of the specific surgical repair and/or as desired.

The surgical anchors of the present disclosure are knotless fixation devices which advantageously minimize or eliminate the need to tie knots to complete the repair. The use of the disclosed surgical anchors also provides secure fixation of the flexible repair strands due to the strands being pushed into the bone hole and held tightly between the outside of the fixation device and the bone hole.

It will be apparent to those skilled in the art having the benefit of the teachings presented in the foregoing descriptions and the associated drawings that modifications, combinations, sub-combinations, and variations can be made without departing from the spirit or scope of this disclosure. Likewise, the various examples described may be used individually or in combination with other examples. Those skilled in the art will appreciate various combinations of examples not specifically described or illustrated herein that are still within the scope of this disclosure. In this respect, it is to be understood that the disclosure is not limited to the specific examples set forth and the examples of the disclosure are intended to be illustrative, not limiting.

As used in this specification and the appended claims, the singular forms “a”, “an” and “the” include plural referents, unless the context clearly dictates otherwise. Similarly, the adjective “another,” when used to introduce an element, is intended to mean one or more elements. The terms “comprising,” “including,” “having” and similar terms are intended to be inclusive such that there may be additional elements other than the listed elements.

Additionally, where a method described above or a method claim below does not explicitly require an order to be followed by its steps or an order is otherwise not required based on the description or claim language, it is not intended that any particular order be inferred. Likewise, where a method claim below does not explicitly recite a step mentioned in the description above, it should not be assumed that the step is required by the claim.

It is noted that the description and claims may use geometric or relational terms, such as proximate, distal, vertical, horizontal, right, left, above, below, upper, lower, top, bottom, linear, arcuate, elongated, parallel, perpendicular, etc. These terms are not intended to limit the disclosure and, in general, are used for convenience to facilitate the description based on the examples shown in the figures. In addition, the geometric or relational terms may not be exact. For instance, walls may not be exactly perpendicular or parallel to one another because of, for example, roughness of surfaces, tolerances allowed in manufacturing, etc., but may still be considered to be perpendicular or parallel.

What is claimed is:

1. A surgical anchor system comprising:

an implant comprising:

a proximal end section configured to releasably engage an end of an inserter, the proximal end section being configured to capture at least one activation strand;

a distal end section that is configured to engage at least one repair strand; and an expander section between the proximal end section and the distal end section, the expander section having a substantially frusto-conical shape that tapers outwardly toward the distal end section and that defines an outer most diameter of the implant; and an expanding cannulated fixation device configured to be loaded on the inserter and to engage the implant, the expanding cannulated fixation device defining at least one longitudinal slot that splits at least a portion of the expanding cannulated fixation device into expandable portions that are configured to expand outwardly, the expandable portions comprising teeth on an inner surface thereof, wherein;

the implant and the expanding cannulated fixation device are configured such that, when i) the implant and the expanding cannulated fixation device are within a hole in a bone with the at least one repair strand engaged with the distal end section and with the at least one activation strand captured by the proximal end section, and ii) force is applied to the at least one activation strand to move the implant proximally relative to the expanding cannulated fixation device, the distal end section holds the at least one repair strand within the hole and the expandable portions expand within the hole to fix the at least one repair strand between the expandable portions and the bone, and the teeth of the expandable portions are configured to engage with the implant when the implant engages with the expanding cannulated fixation device to expand the expandable portions.

2. The surgical anchor system of claim 1, wherein the proximal end section comprises an eyelet for capturing the at least one activation strand.

3. The surgical anchor system of claim 2, wherein the distal end section comprises an eyelet for capturing the at least one repair strand.

4. The surgical anchor system of claim 3, wherein a size of the eyelet in the distal end section is at least about twice a size of the eyelet in the proximal end section.

5. The surgical anchor system of claim 3, wherein the at least one repair strand is suture or suture tape.

6. The surgical anchor system of claim 1, wherein the expanding cannulated fixation device defines at least one longitudinal slot adjacent to the expandable portions.

7. The surgical anchor system of claim 1, wherein the expanding cannulated fixation device comprises bone gripping features.

8. A method of attaching soft tissue to bone with knotless fixation, the method comprising:

installing a first plurality of anchors in a first medial row; and installing a second plurality of anchors in a second lateral row, wherein at least one of the first plurality of anchors or the second plurality of anchors comprises the surgical anchor system of claim 1.

9. A method of attaching soft tissue to bone with knotless fixation using the surgical anchor system of claim 1, the method comprising:

inserting an anchor with a length of suture attached thereto into a first hole in the bone;

passing the suture attached to the first hole through the soft tissue;

positioning the implant, with a free end of the suture threaded through the distal end section, over a second hole in the bone and inserting the implant into the second hole in the bone; and installing the expanding cannulated fixation device into the second hole in the bone, over the implant, to knotlessly secure the suture in the second hole.

10. The method of claim 9, further comprising:

retrieving the suture through a cannula after the suture is passed up through the soft tissue; and inserting, after retrieving the suture through the cannula, the end of the suture through the distal end section.

11. The method of claim 9, further comprising tensioning the suture.

12. A method of tissue repair with knotless fixation using the surgical anchor system of claim 1, the method comprising:

coupling the at least one repair strand to tissue to be fixated;

inserting the implant, with the at least one repair strand extending through the distal end section and with the at least one activation strand extending through the proximal end section, into the hole of the bone;

installing, after inserting the implant into the hole, the expanding cannulated fixation device into the hole with the at least one repair strand arranged between the cannulated fixation device and the bone; and expanding, after installing the expanding cannulated fixation device into the hole, the expandable portions by pulling the at least one activation strand to force the implant into the expanding cannulated fixation device while the expanding cannulated fixation device remains stationary, to compress the expandable portions against the bone with the at least one repair strand disposed between the expandable portions and the bone, and to fix the tissue to the bone without knots.

13. The method of claim 12, further comprising threading an other repair strand through the proximal end section.

14. The method of claim 13, further comprising locking the other repair strand to the proximal end section.

15. The method of claim 14, wherein locking the other repair strand comprises threading a free end of the other repair strand through a splice in the other repair strand.

16. The method of claim 12, wherein the implant and the expandable cannulated fixation device are axially aligned when the at least one activation strand is pulled to force the implant into the expanding cannulated fixation device.

17. The method of claim 12, wherein an eyelet of the distal end section remains outside of expandable cannulated fixation device when the at least one activation strand is pulled to force the implant into the expanding cannulated fixation device.

18. The method of claim 12, further comprising preloading the expandable cannulated fixation device on a shaft of an inserter and releasably attaching the implant to a distal end of the inserter.

19. The surgical anchor system of claim 1, wherein:

the surgical anchor system further comprises:

the at least one activation strand captured by the proximal end section; and the at least one repair strand engaged with the distal end section, the at least one repair strand is threaded through the distal end section and is positioned outside of the expanding cannulated fixation device, and the at least one activation strand is removable from the proximal end section after the implant and the expanding cannulated fixation device are implanted.

20. The surgical anchor system of claim 1, wherein:

the proximal end section of the implant comprises teeth, and the teeth of the expandable portions are configured to engage with the teeth of the proximal end section of the implant when the implant engages with the expanding cannulated fixation device to expand the expandable portions.

* * * * *